United States Patent [19]

Rasmussen

[11] Patent Number: 4,542,144
[45] Date of Patent: Sep. 17, 1985

[54] ANTICONVULSANT N-ARYL-N'-(2-THIAZOLIDINYLIDENE)UREAS

[75] Inventor: Chris R. Rasmussen, Ambler, Pa.

[73] Assignee: McNeilab Inc., Fort Washington, Pa.

[21] Appl. No.: 533,671

[22] Filed: Sep. 19, 1983

Related U.S. Application Data

[63] Continuation-in-part of Ser. No. 321,670, Nov. 16, 1981, abandoned.

[51] Int. Cl.$^4$ ................ C07D 277/18; A61K 31/425
[52] U.S. Cl. ..................................... 514/371; 548/190
[58] Field of Search ........................ 548/190; 424/270

[56] References Cited

PUBLICATIONS

Najer, Bull. Soc. Chim. France, 323, (1963).

Primary Examiner—Robert Gerstl
Attorney, Agent, or Firm—David J. Levy

[57] ABSTRACT

N-aryl-N'-(2-thiazolidinylidene)urea compounds of Formula II

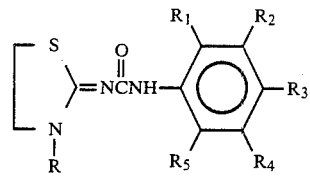

wherein:

R is $CH_3$, $C_2H_5$, or H;
$R_1$ is $CH_3$, $C_2H_5$, Cl, Br, F, $CF_3$, $OCH_3$ or H, provided that $R_1$ is not H where R is H;
$R_2$ is $CH_3$ or H, provided that $R_2$ is not H when R is H;
$R_3$ is H or F or $CH_3$;
$R_4$ is H or $CH_3$;
$R_5$ is $CH_3$, $C_2H_5$, Cl, Br, F, $CF_3$, $OCH_3$, have anticonvulsant activity and are useful in the treatment of epilepsy.

19 Claims, No Drawings

ANTICONVULSANT N-ARYL-N'-(2-THIAZOLIDINYLIDENE)UREAS

This is a continuation-in-part of application Ser. No. 321,670 filed Nov. 16,1981 now abandoned.

FIELD OF THE INVENTION

This invention relates to novel compounds, which are N-aryl-N'-(2-thiazolidinylidene)ureas, shown in Formula II, pharmaceutical compositions containing said compounds in a pharmaceutically acceptable carrier; and to a process for treating mammals having symptoms of epilepsy by administering thereto said pharmaceutical compositions.

DESCRIPTON OF THE PRIOR ART

Compounds are known, which differ from some of those of the present invention either in lacking the N-methyl or -ethyl (3-position) substituent on the thiazolidine ring, or in lacking the required substitution pattern on the phenyl ring where said N-atom of the thiazolidine ring is unsubstituted.

The journal articles discussing said compounds are: (1) D. L. Klayman, J. J. Maul, and G. W. A. Milne, *J. Heterocyclic Chem.* 5, 517 (1968); (2) D. L. Klayman and J. J. Maul, *Tetrahedron Letters*, 281–284 (1967); and (3) H. Najer, R. Giudicelli, J. Menin, and C. Morel, *Bull. Soc. Chim. France*, 323(1963).

No biological activity is disclosed for said prior art compounds, and when some of them were made and tested they proved not to be useful as anticonvulsants when tested in the Maximal Electroshock (MES) test, which is used to show the anticonvulsant utility of the compounds of the present invention.

These known prior art N-aryl-N'-(2-thiazolidinylidene) ureas or tautomers thereof, which are all unsubstituted on the N-atom (3-position) of the thiazolidine ring are depicted in Table I, and have the structure shown in Formula I:

TABLE I

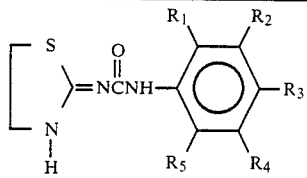

| No. | McN | $R_1$ | $R_2$ | $R_3$ | $R_4$ | $R_5$ | Reference | Mice 45' post dose MES test results Dose (mg/kg p.o.) |
|---|---|---|---|---|---|---|---|---|
| 1 | X-896 | H | H | H | H | H | 1,2,3 | IA[1] (200) |
| 2. | | CH$_3$ | H | H | H | H | 3 | ED$_{50}$ > 200 ED$_{50}$ 232 (173.9–309.8) 30% block at 200 mg/kg |
| 3. | | H | CH$_3$ | H | H | H | 3 | NT[2] |
| 4. | | H | H | CH$_3$ | H | H | 3 | NT[2] |
| 5. | 5589 | H | H | OCH$_3$ | H | H | 3 | IA[1] |
| 6. | | Cl | H | H | H | H | 3 | IA[1] |
| 7. | X-893 | H | Cl | H | H | H | 3 | IA[1] (200) |
| 8. | | H | H | Cl | H | H | 3 | NT[2] |
| 9. | | Cl | H | H | Cl | H | 3 | NT |
| 10. | 5860 | H | Cl | Cl | H | H | 3 | IA[1] |

TABLE I-continued

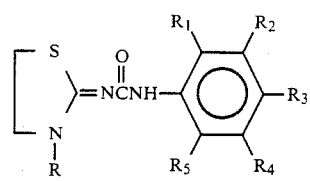

| No. | McN | $R_1$ | $R_2$ | $R_3$ | $R_4$ | $R_5$ | Reference | Mice 45' post dose MES test results Dose (mg/kg p.o.) |
|---|---|---|---|---|---|---|---|---|
| 11. | | H | H | NO$_2$ | H | H | 3 | NT |

[1]IA = inactive, only a 10% block of tonic extension 45' post dose, which is pharmacologically insignificant.
[2]NT = not tested.

SUMMARY OF THE INVENTION

The present invention is directed to N-aryl-N'-(2-thiazolidinylidene)urea derivatives having the structure shown in Formula II:

wherein:
R is CH$_3$, C$_2$H$_5$, or H;
R$_1$ is CH$_3$, C$_2$H$_5$, Cl, Br, F, CF$_3$, OCH$_3$ or H, provided that R$_1$ is not H where R is H;
R$_2$ is CH$_3$ or H, provided that R$_2$ is not H when R is H;
R$_3$ is H, F or CH$_3$;
R$_4$ is H or CH$_3$; and
R$_5$ is CH$_3$, C$_2$H$_5$, Cl, Br, F, CF$_3$, or OCH$_3$.

A preferred group of compounds for purposes of the present invention, are those of Formula II above; wherein:
R is H or CH$_3$;
R$_1$ is H (except when R=H), CH$_3$, C$_2$H$_5$, Cl; Br, F, OCH$_3$ or CF$_3$;
R$_2$ is H;
R$_3$ is H;
R$_4$ is H; and
R$_5$ is CH$_3$, C$_2$H$_5$, Cl, Br, F, OCH$_3$ or CF$_3$.

The presence of either a 2,6-disubstituted phenyl group (R=H or CH$_3$) or a 2-monosubstituted (CH$_3$, Cl, CF$_3$, or OCH$_3$) phenyl group and coupled with a 3-methyl substituent on the thiazolidine ring confers especially important pharmacological properties.

The compound of Formula II are active in the Maximal Electroshock (MES) test, which indicates anticonvulsant activity, and that such compounds are useful for the treatment of epilepsy. Thus, the present invention also relates to a process for treating epilepsy by administering to an animal in need of such treatment a pharmaceutical composition containing a therapeutically sufficient amount of said compound of Formula II and a carrier; and to the aforesaid pharmaceutical composition.

The compounds of the present invention can be prepared by the following reaction scheme:

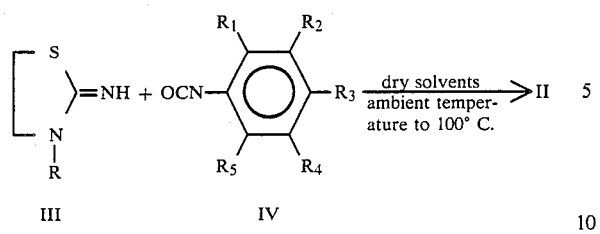

III      IV

The starting materials III are 2-imino-3-(H or CH₃ or C₂H₅)thiazolidines, which are all known in the literature. Many of the substituted phenyl isocyanates IV are known in the literature also, and those that are not can be prepared by the standard procedures well-known in the art.

The reaction is carried out in a dry solvent. Useful solvents include benzene, toluene, xylene and the like (aromatic hydrocarbons), DMF, DMSO, 1-methyl-2-pyrrolidinone, hexamethylphosphoric acid triamide (HMPA), sulfolane and the like (polar aprotic solvents) and THF, dioxane, acetonitrile, acetone, 2-butanone and the like. These reactions may be conveniently carried out from ambient temperatures to about 100° C.

Equimolar ratios of reactants III and IV are used, although a slight stoichiometric excess of III is permissible.

The reaction products II may be purified by standard techniques known in the art, e.g., recrystallization.

The compound of Formula II have been found to have useful pharmacological properties as demonstrated by the Maximal Electroshock (MES) test.

Activity in the MES test, indicating anticonvulsant activity, is characterized by a block of the tonic extensor seizure caused by applying an electric shock to mice via corneal electrodes as described in Swinyard et al., *J. Pharmacol. Exp. Ther.*, 106, 319–330 (1952) and recorded as % block. A more recent description of current practice in anticonvulsant drug screening has also been reported by Swinyard et al., *Epilepsia*, 19, 409–428 (1978).

The results obtained in the MES test are as set forth in Table II.

TABLE II
(New Compounds)

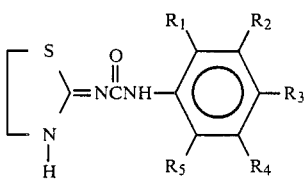

| No. | McN No. | R | $R_1$ | $R_2$ | $R_3$ | $R_4$ | $R_5$ | Mice (45' post dose) MES test results Dose (mg/kg p.o.) |
|---|---|---|---|---|---|---|---|---|
| 1 | 4297 | Me | H | H | H | H | H | IA(100)[1,2] |
| 2 | 4705 | Me | Me | H | H | H | H | ED₅₀(4.8) |
| 3 | 4697 | Me | H | Me | H | H | H | Active, weak (200)[2] 70% block ED₅₀(<200) |
| 4 | 4728 | Me | H | H | Me | H | H | IA(200) |
| 5 | 4698 | Me | Cl | H | H | H | H | Active(200)[2] 70% block ED₅₀(<200) |
| 6 | 4284 | Me | H | H | Cl | H | H | IA(200) |

TABLE II-continued
(New Compounds)

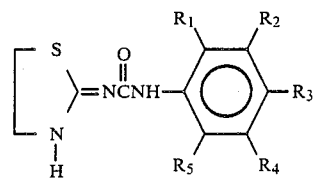

| No. | McN No. | R | $R_1$ | $R_2$ | $R_3$ | $R_4$ | $R_5$ | Mice (45' post dose) MES test results Dose (mg/kg p.o.) |
|---|---|---|---|---|---|---|---|---|
| 7 | 4729 | Me | H | H | Cl | H | H | IA(200) |
| 8 | 4696 | Me | OMe | H | H | H | H | ED₅₀(235.4) |
| 9 | 4699 | Me | H | OMe | H | H | H | Active(200)[2] 80% block ED₅₀(<200) |
| 10 | 4739 | Me | H | H | OMe | H | H | IA(200) |
| 11 | 4702 | Me | CF₃ | H | H | H | H | ED₅₀(92.2) |
| 12 | 4703 | Me | H | CF₃ | H | H | H | IA(200) |
| 13 | 4712 | Me | H | H | CF₃ | H | H | IA(200) |
| 14 | 4737 | Me | H | H | NO₂ | H | H | IA(200) |
| 15 | 4701 | Me | Et | H | H | H | Et | ED₅₀(14.2) |
| 16 | 4690 | Me | Et | H | H | H | Me | ED₅₀(17.4) |
| 17 | 4258 | H | Me | H | H | H | Me | ED₅₀(31) 3-Me (Compd. No. 18) 2.6× more potent than 3-H |
| 18 | 4278 | Me | Me | H | H | H | Me | ED₅₀(11.8) |
| 19 | 4726 | Me | Me | H | H | Me | H | ED₅₀(66.1) |
| 20 | 4715 | Me | Me | H | Me | H | H | ED₅₀(178.3) |
| 21 | 4717 | Me | Me | Me | H | H | H | ED₅₀(37.2) |
| 22 | 4714 | Me | H | Me | Me | H | H | Active [very weak] ED₅₀(>200); 10% block |
| 22a | 5864 | H | H | Me | Me | H | H | IA |
| 23 | 4723 | Me | H | Me | H | Me | H | IA(200) |
| 24 | 4688 | Me | H | CF₃ | H | CF₃ | H | IA(200) |
| 25 | 4687 | Me | Me | H | Me | H | Me | ED₅₀(66.51) |
| 26 | 4680 | Me | Cl | H | H | H | Me | ED₅₀(15.26) |
| 27 | 4259 | H | Cl | H | H | H | Cl | ED₅₀(70.7) 3-Me (Compd. No. 28) 4× more potent than 3-H |
| 28 | 4273 | Me | Cl | H | H | H | Cl | ED₅₀(17.4) |
| 29 | 4765 | Me | F | H | H | H | F | ED₅₀(22.7) |
| 30 | 4743 | Me | Br | H | H | H | Br | ED₅₀(69.6) |
| 31 | 4752 | Me | Br | H | F | H | Br | Active(200)[2] 80% block ED₅₀(<200) |
| 32 | 4686 | Me | Cl | H | Cl | H | Cl | IA(200) |
| 33 | 4749 | Me | OMe | H | H | H | OMe | ED₅₀(41.2) |
| 34 | 4754 | Me | H | OMe | OMe | H | H | Active [very weak] (200)[2] 20% block; ED₅₀(>200) |

[1]IA = Inactive
[2]Only dose tested

When the N-atom (3-position) of the thiazolidine ring is unsubstituted (R=H), the phenyl ring must be 2,6-disubstituted in order to obtain useful anticonvulsant activity. Compare entry 10, Table I, with entry 27, Table II, and entry 22a with entry 17, Table II. These NH compounds are surprisingly more potent than the disubstituted prior art and prior art-like compounds. When the 3-position of the thiazolidine ring is substituted with CH₃, the compounds become on the order of 3-4 times or more potent than the corresponding NH compounds. Compare entry 17 with entry 18 and entry 27 with entry 28 (all Table II). Thus, even some monosubstituted phenyl compounds show useful anticonvulsant activity compared with the corresponding prior art compounds (σ-Cl or CH₃).

For treating epilepsy compounds of Formula II may be employed at a daily dosage range of from 30 to 2000 mg usually in 2-4 divided doses. A unit dose is expected to contain from about 10-500 milligrams of the active ingredient.

To prepare the pharmaceutical compositions of this invention, an N-aryl-N'-2-thiazolidinylidene)urea compound of Formula II, as the active ingredient, is intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For suppositories, the carrier will usually comprise coca butter. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, suppository, teaspoonful and the like, from about 10 to about 500 mg of the active ingredient.

The foregoing compositions are particularly suitable for use in the treatment of convulsions or epilepsy or the symptoms of epilepsy by a method comprising internally administering to a subject suffering from the symptoms of epilepsy compositions comprising an effective epilepsy inhibiting amount of a compound of Formula I.

The following examples illustrate the invention, but are not to be construed as limiting.

EXAMPLE I

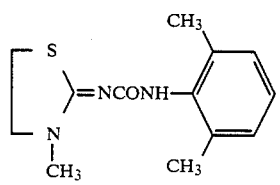

N-(2,6-dimethylphenyl)-N'-(3-methyl-2-thiazolidinylidene)urea-McN-4278

A solution of 4.41 g (0.030 mole) of 2,6-dimethylphenylisocyanate in 30 ml of dry DMF was added dropwise over a period of 30 minutes to a solution of 3.50 g (0.030 mole) of 2-imino-3-methylthiazolidine in 30 ml of dry DMF. The reaction mixture was stirred at room temperature for four hours, poured into water and the crude product was filtered. Two recrystallization from benzene-hexane gave 6.0 g (76%) of analytically pure product; m.p. 166°-167° C.

Calc'd for $C_{13}H_{17}N_3OS$: C, 59.29; H, 6.50; N, 15.95; Found: C, 59.15; H, 6.51; N, 15.92; UV Max (MeCN): 248.5 nm (ε25,900); IR(KBr): 3420(b); 3260; 3170; 3020; 2950; 2930; 2870; 1628; 1565 cm⁻¹.

EXAMPLE II

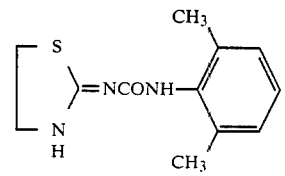

N-(2,6-dimethylphenyl)-N'-(2-thiazolidinylidene)urea-McN-4258

A solution of 8.82 g (0.060 mole) of 2,6-dimethylphenylisocyanate in 60 ml of dry DMF was added dropwise to a solution of 6.0 g (0.060 mole) of 2-aminothiazoline in 50 ml of dry DMF. The reaction mixture was stirred at room temperature for 3 hours, poured into water and the crude product was filtered to give 8.0 g (53%) of crude product.

Two recrystallization from THF-Et₂O gave the analytically pure product; m.p. 176°-178° C. (soft, then solidifies and melts at 267°-276° C.).

Calc'd for $C_{12}H_{15}N_3OS$: C, 57.81; H, 6.06; N, 16.85; Found: C, 57.84; H, 6.10; N, 16.76; UV Max (MeOH): 246.5 nm (ε19,700); IR (NUJOL): 3210 (sh); 3100 (sh); 2940 (b); 2850; 1675; 1635; 1630 cm⁻¹; NMR (DMSO-d₆): δ8.73 (s, 1.9 2NH); 7.08 (s, 3.0 aromatic H); 3.82-2.78 (m, 4.0 H, $SCH_2CH_2N$—); 2.18 (s, 6H, 2CH₃).

EXAMPLE III

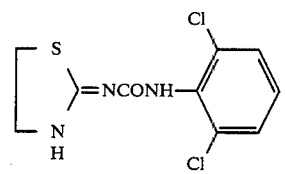

N-(2,6-dichlorophenyl)-N'-(2-thiazolidinylidene)urea-McN-4259

A solution of 11.28 g (0.060 mole) of 2,6—dichlorophenyl isocyanate in 30 ml of dry benzene was filtered from some insolubles directly into an addition funnel, and the filtrate was added dropwise to a solution of 6.13 g (0.060 mole) of 2-aminothiazoline in 80 ml of dry DMF. The reaction mixture was stirred at room temperature for three hours, then the benzene was evaporated in vacuo at room temperature, and the residue was poured into water. The crude product was filtered and recrystallized twice from THF-Et₂O to give 9.6 g (55%) of white solid; m.p. 174°-175.5° C.

Calc'd for $C_{10}H_9Cl_2N_3OS$: C, 41.39; H, 3.13; N, 14.98; Found: C, 41.46; H, 3.13; N, 14.48; UV Max (MeOH): 228 (ε15,900); 249 nm (ε21,300); IR(KBr):

3360; 3225; 3205; 3100; 2940(b); 2860; 1685; 1630 cm⁻¹; NMR(DMSO-d₆): δ8.62 (s, 2.0, NH); 7.50–7.10 (m, 3.0H, aromatic); 3.50 (t, J=7 Hz, 2H, NC$\underline{H}_2$—); 3.09 (t, J=7 Hz, 2H, S-C$\underline{H}_2$—).

EXAMPLE IV

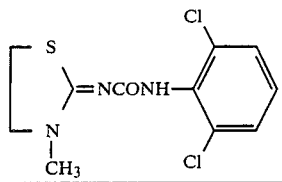

N-(2,6-dichlorophenyl)-$\underline{N}$'-(3-methyl-2-thiazolidinylidene)urea—McN-4273

A solution of 8.1 g (0.043 mole) of 2,6-dichlorophenyl isocyanate in 30 ml of dry benzene, was filtered from some insolubles directly into an addition funnel, then was added dropwise to a solution of 5.0 g (0.043 mole) of 2-imino-3-methylthiazolidine in 50 ml of dry DMF. The reaction mixture was stirred at room temperature for 4 hours, the benzene was evaporated in vacuo at room temperature, and the residue was poured into water. The crude product was filtered, and recrystallized twice from DMF-H₂O to give 9.9 g (76%) of pure product; m.p. 178.5°–181.5° C.

Calc'd for C₁₁H₁₁Cl₂N₃OS: C, 43.43; H, 3.64; N, 13.81; Found: C, 43.88; H, 3.50; N, 13.95; UV Max (MeCN): 252 nm (ε25,100).

EXAMPLES V–XX

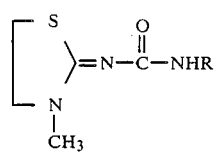

2-Thiazolidinylidene Ureas A General Method

A solution of 0.50 mole of 2-imino-3-methylthiazolidine in 200 ml of ether[1] was treated with a solution of 0.50 mole of the appropriate substituted phenylisocyanate in about 30 ml of ether, stoppered and stirred for about 24 hours[2], filtered and recrystallized[3] to yield the corresponding ureas listed in Table III.

(1) The free base was liberated from the hydroiodide salt via basification with 50% sodium hydroxide followed by extraction into ether and drying over anhydrous K₂CO₃. (2) Reaction time varied, mostly as a matter of convenience. Twenty-four hours is sufficient time for all compounds listed. (3) The pure products are usually obtained after one or two recrystallizations.

TABLE III

| Ex. No. | R | Empirical Formula | % Yield | m.p. (°C.) | Recryst. Solv. | UV max MeOH (nm) (ε) K = 1000 | ANAL. Calc'd C | H | N | Found C | H | N | McN No. |
|---|---|---|---|---|---|---|---|---|---|---|---|---|---|
| V | 2-Et—6-MePh | C₁₄H₁₉N₃OS | 50.5 | 106–108 | E/Hex | 249(26.2K) | 60.62 | 6.90 | 15.15 | 60.52 | 6.95 | 15.13 | 4690 |
| VI | 2,4,6-TriMePh | C₁₄H₁₉N₃OS | 92.3 | 135–136 | MC/MCH | 249(26.9K) | 60.62 | 6.90 | 15.15 | 60.59 | 6.92 | 15.14 | 4687 |
| VII | 2-ClPh | C₁₁H₁₂ClN₃OS | 77.2 | 161.5–162.5 | MC/E | 271(31K) | 48.98 | 4.48 | 15.58 | 48.99 | 4.52 | 15.57 | 4698 |
| VIII | 2-MeOPh | C₁₂H₁₅N₃O₂S | 84.8 | 158–159.5 | Mc/E | 265(23.5K) 272.5(25.3K) 291(21.5K) | 54.32 | 5.70 | 15.84 | 54.33 | 5.73 | 15.85 | 4696 |
| IX | 2-MePh | C₁₂H₁₅N₃OS | 73.0 | 147–149 | MC/E | 259(24.1K) | 57.81 | 6.06 | 16.85 | 57.93 | 6.09 | 16.83 | 4705 |
| X | 2,4-DiMePh | C₁₃H₁₇N₃OS | 69.4 | 114–116 | MC/E | 257(23.6K) | 59.29 | 6.51 | 15.96 | 59.30 | 6.51 | 15.96 | 4715 |
| XI | 2,3-DiMePh | C₁₃H₁₇N₃OS | 80.5 | 166–168 | MC/E | 255.5(23.8K) | 59.29 | 6.51 | 15.86 | 59.22 | 6.56 | 15.93 | 4717 |
| XII | 2,5-DiMePh | C₁₃H₁₇N₃OS | 74.3 | 134–136 | MC/E | 260(23.1K) | 59.29 | 6.51 | 15.96 | 59.28 | 6.54 | 15.95 | 4726 |
| XIII | 3,5-DiMePh | C₁₃H₁₇N₃OS | 68.7 | 143.5–157.5 | MC/E | 274.5(29.5K) | 59.29 | 6.51 | 15.96 | 59.27 | 6.55 | 15.94 | 4723 |
| XIV | 2,6-DiBrPh | C₁₁H₁₁Br₂N₃OS | 66.7 | 173–175 | MC/E | 251.5(24.5K) | 33.61 | 2.82 | 10.69 | 33.59 | 2.86 | 10.65 | 4743 |
| XV | 2-Cl—6-MePh | C₁₂H₁₄ClN₃OS | 73.0 | 157–158 | MC/T | 251(26.6K) | 50.79 | 4.97 | 14.81 | 50.83 | 5.01 | 14.76 | 4680 |
| XVI | 2,6-DiEtPh | C₁₅H₂₁N₃OS | 37.0 | 85–87 | E | 248(26.0K) | 61.83 | 7.26 | 14.42 | 61.80 | 7.30 | 14.42 | 4701 |
| XVII | 2-CF₃Ph | C₁₂H₁₂F₃N₃OS | 40.0 | 111–112 | EA | 264(27.2K) | 47.52 | 3.99 | 13.85 | 47.52 | 3.99 | 13.85 | 4702 |
| XVIII | 2,6-Br₂—4-FPh | C₁₁H₁₀Br₂FN₃OS | 50 | 163–164 | EtOAc | 251(25.2K) | 32.14 | 2.45 | 10.22 | 32.27 | 2.48 | 10.22 | 4752 |
| XIX | 2,6-DiFPh | C₁₁H₁₁F₂N₃OS | 30 | 164.5–165.5 | EtOAc | 253(28.8K) | 48.70 | 4.09 | 15.49 | 48.78 | 4.09 | 15.48 | 4765 |
| XX | 2,6-DiMeOPh | C₁₃H₁₇N₃O₃S | 78 | 158–160 | MC/E | 253(23.9K) | 52.87 | 5.80 | 14.23 | 52.84 | 5.82 | 14.23 | 4749 |

EXAMPLE XXI

By following the teachings of Example II, but substituting an appropriate 2,6-disubstituted phenyl isocyanate for the 2,6-dimethyl phenyl isocyanate employed therein, there can be produced the following II (R=H):

1. $\underline{N}$-(2-chloro-6-methyl)phenyl-$\underline{N}$'-(2thiazolidinylidene)-urea.
2. $\underline{N}$-(2,6-dibromo)phenyl-$\underline{N}$'-(2-thiazolidinylidene)urea.
3. $\underline{N}$-(2,6-dimethoxy)phenyl-$\underline{N}$'-(2-thiazolidinylidene)urea.
4. $\underline{N}$-(2-methoxy-6-methyl)phenyl-$\underline{N}$'-(2-thiazolidinylidene)urea.
5. $\underline{N}$-(2-methyl-6-trifluoromethyl)phenyl-$\underline{N}$'-(2-thiazolidinylidene)urea.
6. $\underline{N}$-(2methoxy-6-trifluoromethyl)phenyl-$\underline{N}$'-(2-thiazolidinylidene)urea.
7. $\underline{N}$-(2-chloro-6-trifluoromethyl)phenyl-$\underline{N}$'-(2-thiazolidinylidene)urea.
8. $\underline{N}$-(2,6-bis-trifluoromethyl)phenyl-$\underline{N}$'-(2-thiazolidinylidene)urea.
9. $\underline{N}$-(2-chloro-6-methoxy)phenyl-$\underline{N}$'-(2-thiazolidinylidene)urea.
10. $\underline{N}$-(2-chloro-6-fluoro)phenyl-$\underline{N}$'-(2-thiazolidinylidene)urea.

EXAMPLE XXII

By following the teachings of Example I, but substituting an appropriate 2,6-disubstituted phenylisocyanate for the 2,6-dimethylphenylisocyante employed therein, there can be produced the following compounds, II (R=CH₃):

1. N-(2-methoxy-6-methyl)phenyl-N'-(3-methyl-2-thiazolidinylidene)urea.
2. N-(2-chloro-6-methoxy)phenyl-N'-(3-methyl-2-thiazolidinylidene)urea.
3. N-(2-chloro-6-trifluoromethyl)phenyl-N'-(3-methyl-2-thiazolidinylidene)urea.
4. N-(2-methoxy-6-trifluoromethyl)phenyl-N'-(3-methyl-2-thiazolidinylidene)urea.
5. N-(2,6-bis-trifluoromethyl)phenyl-N'-(3-methyl-2-thiazolidinylidene)urea.
6. N-(2-methyl-6-trifluoromethyl)phenyl-N'-(3-methyl-2-thiazolidinylidene)urea.
7. N-(2-chloro-6-fluoro)phenyl-N'-(3-methyl-2-thiazolidinylidene)urea.

EXAMPLE XXIII

By following the teachings of Example I, but substituting an equimolar amount of 3-ethyl-2-iminothiazolidine for the 2-imino-3-methylthiazolidine and by substituting an appropriate 2,6-disubstituted phenylisocyanate for the 2,6-dimethylphenylisocyanate, there may be produced the following ureas of Formula II (R=Et).

N-(2,6-dimethyl)phenyl-N'-(3ethyl-2-thiazolidinylidene)urea.

N-(2-chloro-6-methyl)phenyl-N'-(3-ethyl-2-thiazolidinylidene)urea.

N-(2,6-dichloro)phenyl-N'-(3-ethyl-2-thiazolidinylidene)urea.

N-(2,6-dimethoxy)phenyl-N'-(3-ethyl-2-thiazolidinylidene)urea.

N-(2-methoxy-6-methyl)phenyl-N'-(3-ethyl-2-thiazolidinylidene)urea.

N-(2-chloro-6-fluoro)phenyl-N'-(3ethyl-2-thiazolidinylidene)urea.

N-(2-ethyl-6-methyl)phenyl-N'-(3-ethyl-2-thiazolidinylidene)urea.

N-(2-methyl-6-trifluoromethyl)phenyl-N'-(3-ethyl-2-thiazolidinylidene)urea.

N-(2-chloro-6-trifluoromethyl)phenyl-N'-(3-ethyl-2-thiazolidinylidene)urea.

N-(2-methoxy-6-trifluoromethyl)phenyl-N'-(3-ethyl-2-thiazolidinylidene)urea.

N-(2,6-bis-trifluoromethyl)phenyl-N'-(3-ethyl-2-thiazolidinylidene)urea.

N-(2,6-dibromo)phenyl-N'-(3-ethyl-2-thiazolidinylidene)urea.

EXAMPLE XXIV

One thousand (1,000) hard gelatin capsules, each containing 200 milligrams of active ingredient, which is N-(2,6-dimethylphenyl)N'-(3-methyl-2-thiazolidinylidene)urea or alternatively the compound of any previous example can be prepared from the following formulation:

|  | Grams |
| --- | --- |
| Active ingredient | 200 |
| Starch | 100 |
| Lactose | 150 |
| Talc | 50 |
| Calcium stearate | 5 |

A uniform mixture of the ingredients can be prepared by blending and employed to fill two-piece hard gelatin capsules. The capsules are suitable to be orally administered to subjects with convulsive disorders.

EXAMPLE XXV

Gelatin capsules can be prepared as described in Example XXIV except that in the formulation, 400 grams of N-(2-chloro-6-methylphenyl)-N'-(3-methyl-2-thiazolidinylidene)urea as active agent providing capsules containing 400 milligrams of said active agent.

EXAMPLE XXVI

One thousand (1,000) compressed tablets, each containing 500 milligrams of N-(2,6-dichlorophenyl)-N'-(3-methyl-2-thiazolidinylidene)urea as the active ingredient can be prepared from the following formulation:

|  | Grams |
| --- | --- |
| Active ingredient | 500 |
| Starch | 75 |
| Microcrystalline cellulose | 100 |
| Calcium stearate | 5 |

The finely powdered ingredients are to be mixed well and granulated with 10 percent starch paste. The granulation is to be dried and compressed into tablets using starch as a disintegrant and calcium stearate as a lubricant.

EXAMPLE XXVII

Parenteral formulations, for intramuscular administration can be prepared as follows:

One thousand (1,000) 1 ml vials, each containing 50 milligrams of active ingredient, which is N-(2,6-dimethylphenyl)-N'-(3-methyl-2-thiazolidinylidene)urea can be prepared from the following formulation:

|  | Quantity |
| --- | --- |
| Active ingredient | 50 grams |
| Benzyl alcohol | 9 grams |
| Povidone | 20 grams |
| Water for injection, q.s. | 1000 ml |

EXAMPLE XXVIII

One thousand (1,000) two gram cocoa butter suppositories, each containing 200 milligrams of active ingredient, which is N-(2,6-dimethylphenyl)-N'-(3-methyl-2-thiazolidinylidene)urea can be prepared from the following formulation:

|  | Quantity |
| --- | --- |
| Active ingredient | 200 grams |
| Cocoa butter | 1800 grams |

EXAMPLE XXIX

N-(3,4-dimethylphenyl)-N'-(2-thiazolidinylidene)urea McN-5864 [Table II, Compound 22a].

Following the method of Example 2, but using 3,4-dimethylphenyl isocyanate instead of the 2,6-dimethylphenyl isocyanate of Example 2, the title compound was obtained, m.p. 155°–156° C.

Calc'd for $C_{12}H_{15}N_3OS$: C, 57.81; H, 6.06; N, 16.85; Found: C, 57.74; H, 6.09; N, 16.85; UV Max (MeOH): 272 nm ($\epsilon$23, 188).

I claim:

1. An N-aryl-N'-(2-thiazolidinylidene)urea derivative selected from the group consisting of:
N-(2,6-dimethylphenyl)-N'-(3-methyl-2-thiazolidinylidene)urea,
N-(2,6-dichlorophenyl)-N'-(3-methyl-2-thiazolidinylidene)urea,
N-(2-methoxyphenyl)-N'-(3-methyl-2-thiazolidinylidene)urea,
N-(2-trifluoromethylphenyl)-N'-(3-methyl-2-thiazolidinylidene)urea,
N-(2,6-diethylphenyl)-N'-(3-methyl-2-thiazolidinylidene)urea,
N-(2-ethyl-6-methylphenyl)-N'-(3methyl-2-thiazolidinylidene)urea,
N-(2,5-dimethylphenyl)-N'-(3-methyl-2-thiazolidinylidene)urea,
N-(2,4-dimethylphenyl)-N'-(3-methyl-2-thiazolidinylidene)urea,
N-(2,3-dimethylphenyl)-N'-(3-methyl-2-thiazolidinylidene)urea,
N-(2,4,6-trimethylphenyl)-N'-(3-methyl-2-thiazolidinylidene)urea,
N-(2-chloro-6-methylphenyl)-N'-(3-methyl-2-thiazolidinylidene)urea.
N-(2,6-difluorophenyl)-N'-(3-methyl-2-thiazolidinylidene)-urea,
N-(2,6-dibromophenyl)-N'-(3-methyl-2-thiazolidinylidene)urea,
N-(2,6-dibromo-4-fluorophenyl)-N'-(3-methyl-2-thiazolidinylidene)urea,
N-(2,6-dimethoxyphenyl)-N'-(3-methyl-2-thiazolidinylidene)urea, and
N-(2,6-dimethylphenyl)-N'-(2-thiazolidinylidene)urea.

2. A compound of claim 1 which is N-(2,6-dimethylphenyl)-N'-(-3-methyl-2-thiazolidinylidene)urea.

3. A compound of claim 1 which is N-(2,6-dichlorophenyl)-N'-(3-methyl-2-thiazolidinylidene)urea.

4. A compound of claim 1 which is N-(2-methoxyphenyl)-N'-(3-methyl-2-thiazolidinylidene)urea.

5. A compound of claim 1 which is N-(2-trifluoromethylphenyl)-N'-(3-methyl-2-thiazolidinylidene)urea.

6. A compound of claim 1 which is N-(2,6-diethylphenyl)-N'-(3-methyl-2-thiazolidinylidene)urea.

7. A compound of claim 1 which in N-(2-ethyl-6-methylphenyl)-N'-(3-methyl-2-thiazolidinylidene)urea.

8. A compound of claim 1 which is N-(2,5-dimethylphenyl)-N'-(3-methyl-2-thiazolidinylidene)urea.

9. A compound of claim 1 which is N-(2,4-dimethylphenyl)-N'-(3-methyl-2-thiazolidinylidene)urea.

10. A compound of claim 1 which is N-(2,3-dimethylphenyl)-N'-(3-methyl-2-thiazolidinylidene)urea.

11. A compound of claim 1 which is N-(2,4,6-trimethylphenyl)-N'-(3-methyl-2-thiazolidinylidene)urea.

12. A compound of claim 1 which is N-(2-chloro-6-methylphenyl)-N'-(3-methyl-2-thiazolidinylidene)urea.

13. A compound of claim 1 which is N-(2,6-difluorophenyl)-N'-(3-methyl-2-thiazolidinylidene)urea.

14. A compound of claim 1 which is N-(2,6-dibromophenyl)-N'-(3-methyl-2-thiazolidinylidene)urea.

15. A compound of claim 1 which is N-(2,6-dibromo-4-fluorophenyl)-N'-(3methyl-2-thiazolidinylidene)urea.

16. A compound of claim 1 which s N-(2,6-dimethoxyphenyl)-N'-(3-methyl-2-thiazolidinylidene)urea.

17. A compound of claim 1 which is N-(2,6-dimethylphenyl)-N'-(2-thiazolidinylidene)urea.

18. A method of treating the symptoms of epilepsy in a mammal requiring such treatment by internally administering thereto an effective epilepsy-inhibiting amount of a pharmaceutical composition comprising as the active ingredient a compound of claim 1 together with a pharmaceutically acceptable carrier wherein the active ingredient is present in unit dosage amount of 10–500 mg.

19. A method according to claim 18 wherein the pharmaceutical composition is administered at daily dosage range of 30 to 2000 mg.

* * * * *